United States Patent [19]
Mayer et al.

[11] Patent Number: 5,834,479
[45] Date of Patent: Nov. 10, 1998

[54] METHOD AND COMPOSITION FOR ALLEVIATING PAIN

[76] Inventors: David J. Mayer, 502 Honaker Ave., Richmond, Va. 23226; Donald D. Price, 3316 Loxley Rd., Richmond, Va. 23227; Jianren Mao, 1630 Monument Ave., Richmond, Va. 23220; John W. Lyle, 28 Inlet Ter., Belmar, N.J. 07719

[21] Appl. No.: 746,202

[22] Filed: Nov. 6, 1996

Related U.S. Application Data

[63] Continuation of Ser. No. 300,736, Sep. 2, 1994, abandoned, which is a continuation-in-part of Ser. No. 95,107, Jul. 21, 1993, which is a continuation-in-part of Ser. No. 27,177, Mar. 5, 1993, Pat. No. 5,352,683.

[51] Int. Cl.[6] .................................................. A61K 31/485
[52] U.S. Cl. ........................ 514/289; 514/825; 514/886
[58] Field of Search .................... 514/289, 886, 514/825

[56] References Cited

U.S. PATENT DOCUMENTS

| | | | |
|---|---|---|---|
| 4,316,888 | 2/1982 | Nelson | 424/127 |
| 4,446,140 | 5/1984 | Nelson | 424/260 |
| 4,593,044 | 6/1986 | Metz | 514/557 |
| 4,777,174 | 10/1988 | Sunshine et al. | 514/264 |
| 4,994,467 | 2/1991 | Zimmerman | 514/288 |
| 5,013,540 | 5/1991 | Redburn | 514/289 |
| 5,096,926 | 3/1992 | Fiorini et al. | 514/569 |
| 5,128,373 | 7/1992 | Fiorini et al. | 514/569 |
| 5,164,398 | 11/1992 | Sims et al. | 514/282 |
| 5,183,807 | 2/1993 | della Valle et al. | 514/25 |

FOREIGN PATENT DOCUMENTS

| | | |
|---|---|---|
| 0081823 | 6/1983 | European Pat. Off. . |
| 0516297 | 12/1992 | European Pat. Off. . |
| 0529898 | 3/1993 | European Pat. Off. . |
| 2082456 | 3/1982 | United Kingdom . |
| 2251616 | 7/1992 | United Kingdom . |
| WO 88/01869 | 3/1988 | WIPO . |
| 94/000124 | 1/1994 | WIPO . |

OTHER PUBLICATIONS

Haley et al., "Evidence for Spinal N–methyl–D–aspartate receptor involvement in prolonged chemical nociception in the rat", Brain Research, 518 (1990), pp. 218–226.

Dickenson et al. "Antagonism at the glycine site on the NMDA receptor reduces spinal nociception in the rat", Neuroscience Letters, 121 (1991), pp. 263–266.

Coderre et al., "The Contribution of Excitatory Amino Acids to Central Sensitization and Persistent Nociception after Formalin–induced Tissue Injury", The Journal of Neuroscience, Sep. 1992, 12 (9), pp. 3665–3670.

Kehne et al., "NMDA receptor complex anatagonists have potential anxiolytic effects as measured with separation–induced ultrasonic vocalizations", European Journal of Pharmacology, 193 (1991), pp. 283–292.

European Search Report dated Jul. 11, 1994 for Application No. EP 94 10 3212.

Brain Res., vol. 588, No. 1, 1992, pp. 144–149.

Neurosci. Lett., vol. 140, No. 2, 1992, pp. 181–184.

*Primary Examiner*—Shailendra Kumar
*Attorney, Agent, or Firm*—Dilworth & Barrese

[57] ABSTRACT

The analgesic effectiveness of an NSAID is significantly enhanced by administering the NSAID prior to, with or following the administration of an analgesia enhancer which is a nontoxic NMDA receptor blocker and/or a nontoxic substance that blocks at least one major intracellular consequence of NMDA receptor activation.

6 Claims, 6 Drawing Sheets

Fig. 6

METHOD AND COMPOSITION FOR ALLEVIATING PAIN

This is a continuation divisional of application Ser. No. 08/300,736, filed on Sep. 2, 1994; now abandoned, which is a continuation-in-part of application Ser. No. 08/095,107 filed Jul. 21, 1993 which in turn is a continuation-in-part of application Ser. No. 08/027,177 filed Mar. 5, 1993, now U.S. Pat. No. 5,352,683.

BACKGROUND OF THE INVENTION

This invention relates to a method and composition for alleviating pain. More particularly, this invention is directed to a method of alleviating pain, e.g., arthritic pain, lumbosacral pain, musculo-skeletal pain, pain associated with a sore throat, etc., by administering to a mammal in need of relief from pain a nonsteroidal antiinflammatory drug (NSAID) such as aspirin or ibuprofen and, as an analgesia enhancer, a nontoxic antagonist for the N-methyl-D-aspartate receptor, e.g., a morphinan such as dextromethorphan or dextrorphan, or a substance that blocks a major intracellular consequence of N-methyl-D-aspartate receptor activation, e.g., a ganglioside such as ganglioside $GM_1$ or ganglioside $GT_{1b}$.

Non-narcotic analgesics such as the NSAIDs, a broad category of drugs which includes aspirin, ibuprofen, flurbiprofen, and the like, are well known for their analgesic and antiinflammatory properties. However, all of the NSAIDS have a tendency to cause gastrointestinal side effects ranging from the relatively mild (dyspepsia and heartburn) to quite severe (ulceration of the stomach or duodenum). The risk of these adverse effects and their severity may increase substantially where their long-term administration is concerned. This is particularly the case with arthritic pain which may require an extended period of analgesia. Were the analgesic activity of the NSAIDs to be significantly enhanced, the dosage levels of these drugs could be decreased thus improving their safety at no loss to their analgesic effectiveness.

Dextromethorphan is the d-isomer of the codeine analog of levorphanol. Unlike the l-isomer, dextromethorphan is said to have no analgesic or addictive properties (Goodman and Gilman's, "The Pharmacological Basis of Therapeutics", 8th ed., McGraw-Hill, Inc. (1990), p. 518). The antitussive activity of dextromethorphan has led to its use in a variety of over-the-counter orally administered therapeutic compositions (tablets, syrups) for the relief of cold, influenza and/or cough conditions. Many, if not most, of these therapeutics also contain a non-narcotic analgesic such as an NSAID. Thus, e.g., U.S. Pat. No. 5,164,398 discloses various oral dosage forms of a therapeutic composition containing (S)-ibuprofen in the form of its (S)-lysine salt as the analgesic component and dextromethorphan in the form of its hydrobromide salt as the antitussive component and the use of the composition to treat pain and/or inflammation in a subject exhibiting a cold, influenza and/or cough condition.

U.S. Pat. No. 4,446,140 describes a method of treating mouth pain, i.e., pain or discomfort associated with the oral cavity, the teeth, gums and other mucosal surfaces of the lips, tongue and mouth resulting from such causes as toothache, denture irritations, canker sores, irritation related to inflamed gums, orthodontic tooth manipulation and appliances, oral surgery, etc., by administration of dextromethorphan alone or together with a conventional analgesic such as acetaminophen, indomethacin, ibuprofen or naproxen or a conventional anesthetic such as benzocaine or butacaine.

European Patent Application 0 081 823 describes a method of temporarily reducing pain and discomfort associated with dysmenorrhea by administration of dextromethorphan alone or in combination with one or more additional drugs, e.g., an analgesic such as acetaminophen, indomethacin, ibuprofen or naproxen.

Heretofore, there has been no recognition or appreciation that the analgesic effectiveness of an NSAID can be appreciably enhanced by administration of the NSAID prior to, with or following the administration of an analgesia-enhancing amount of dextromethorphan. Thus, U.S. Pat. Nos. 5,164,398 and 4,446,140 and European Patent Application 0 081 823 each discloses dosage levels of dextromethorphan that would not be effective for increasing the analgesic effectiveness of any NSAID mentioned therein. While these publications also disclose dosage levels of dextromethorphan that would, as has now been discovered herein, result in enhanced effectiveness of the NSAID, such a result is entirely accidental and fortuitous.

SUMMARY OF THE INVENTION

In accordance with the present invention there is provided a method of alleviating pain which comprises administering to a mammal exhibiting pain (a) an analgesia-inducing amount of an NSAID and (b) an analgesia enhancing amount of at least one analgesia enhancer selected from the group consisting of nontoxic antagonist for the N-methyl-D-aspartate receptor and nontoxic substance that blocks a major intracellular consequence of N-methyl-D-aspartate receptor activation with (a) being administered prior to, with or following the administration of (b).

The method of the invention and the therapeutic composition therefor are applicable to the treatment of all varieties of pain and not just those associated with a cold, influenza, cough, oral pain and/or dysmenorrhea condition as in the prior art. Thus, for a mammal in need of pain relief but not exhibiting any of the foregoing conditions, an enhanced level of analgesia for an equivalent dosage of NSAID, or an equivalent level of analgesia for a reduced dosage of NSAID, can be achieved when the NSAID is administered prior to, with or following the administration of the analgesia enhancer. Furthermore, the method of alleviating pain of this invention and the therapeutic composition which is used in its practice provide highly effective analgesia for a number of pain conditions not even hinted at in the prior art. Thus, e.g., the invention provides significantly greater pain relief for a given dosage of NSAID than that achieved with the NSAID alone for such pain conditions as arthritic pain, lumbosacral pain, musculoskeletal pain, pain associated with a sore throat, and the like, each of which is accompanied by an active site of inflammation.

The expression "N-methyl-D-aspartate receptor" shall be understood to include all of the binding site subcategories associated with the NMDA receptor, e.g., the glycine-binding site, the phenylcyclidine (PCP)-binding site, etc., as well as the NMDA channel. Thus, the invention herein contemplates the use of nontoxic substances that block an NMDA receptor binding site, e.g., dextrorphan, or the NMDA channel, e.g., a source of magnesium such as magnesium sulfate.

The term "nontoxic" as used herein shall be understood in a relative sense and is intended to designate any substance that has been approved by the United States Food and Drug Administration ("FDA") for administration to humans or, in keeping with established regulatory criteria and practice, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 (the compound 5-methyl-10,11-dihydro-SH-dibenze[a,d] cyclohepten-5,10-imine), CPP (the compound 3-[2-carboxypiperazin-4-yl] propyl-1-phosphonic acid) and PCP (the compound 1-(1-phenylcyclohexyl)piperidine) whose toxicities effectively preclude their therapeutic use.

The term "pain-alleviating" shall be understood herein to include the expressions "pain-suppressing" and "pain-inhibiting" as the invention is applicable to the alleviation of existing pain as well as the suppression or inhibition of pain which would otherwise ensue from an imminent pain-causing event.

DESCRIPTION OF THE PREFERRED EMBODIMENTS

Any of the NSAIDs can be used herein. For extensive listings of NSAIDs, see, e.g., Goodman and Gilman's "The Pharmacological Basis of Therapeutics", 8th ed., McGraw-Hill, Inc. (1990), pp. 638–670, "Remington's Pharmaceutical Sciences", 17th ed., Mack Publishing Company (1985), pp. 1116–1122 and U.S. Pat. No. 4,777,174.

Specific NSAIDs that can be used herein include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, their mixtures and their pharmaceutically acceptable salts.

Among the nontoxic substances that block the NMDA receptor and as such are useful as analgesia enhancers herein are dextromethorphan ((+)-3-hydroxy-N-methylmorphinan) and its metabolite dextrorphan ((+)-3-hydroxy-N-methylmorphinan), their mixtures and their pharmaceutically acceptable salts. Other useful nontoxic substances that block the NMDA receptor include memantine, pyrrolo-quinoline quinone and cis-4-(phosphonomethyl)-2-piperidinecarboxylic acid. Of the NMDA receptor antagonists, dextromethorphan in the form of its hydrobromide salt is preferred for use herein due to its high degree of proven safety and its ready availability. While dextrorphan and its pharmaceutically acceptable salts will also provide excellent results, it is not known to be in commercial manufacture at this time.

In addition to, or in place of, a blocker for the NMDA receptor, at least one nontoxic substance that blocks a major intracellular consequence of NMDA receptor activation can also be used as the analgesia enhancer herein. Activation of the NMDA receptor, a subtype of excitatory amino acid receptors, induces a number of changes in the functional activity of nerve cells and, in particular, their capacity for excitability or inhibition in the presence of an addictive substance via an increase in intracellular Ca++ concentration. The major consequences of NMDA receptor activation include the following sequences, or cascades, of events occurring within nerve cells:

a) translocation and activation of protein kinases such as protein kinase C→phosphorylation of substrate proteins such as cytosolic enzymes, channel proteins, receptor proteins, etc.→changes in functional activity;

b) initiation of early gene (c-fos, c-jun, zif-268, etc.) expression by either increased intracellular Ca++ or Ca++-activated protein kinases→expression of functional genes responsible for production of cellular enzymes (such as protein kinases), receptor proteins (such as the NMDA receptor), ion channel proteins (such as K+, Na+, Ca++ channels), neuropeptides (such as dynorphin), etc.→changes in functional activity;

c) Ca++/calmodulin (or other Ca++ binding proteins) induced activation of enzymes and other cellular components→activation of Ca++/calmodulin-protein kinase systems such as Ca++/calmodulin kinase II→autophosphorylation of enzymes (e.g., Ca++/calmodulin kinase II) or other functional proteins→changes in functional activity;

d) Ca++/calmodulin induced activation of constitutive nitric oxide synthase as well as induction of inducible nitric oxide synthase→production of nitric oxide→i) production of cyclic guanosine monophosphate via activation of guanosine cyclase resulting in activation of protein kinases and early gene expression; ii) direct protein modification such as enzymes, receptor and/or channel proteins; iii) lipid membrane modification and/or nucleic acid modification via scavenge of free radicals; iv) induction of neurotoxicity at higher nitric oxide levels; v) retrograde actions in adjacent neurons or glial cells such as facilitation of glutamate release/NMDA receptor activation and/or inhibition of post-synaptic NMDA receptors→changes in functional activity;

e) interactions with the cyclic adenosine monophosphate/protein kinase A system, the phospholipase C-inositol triphosphate-Ca++/diacylglycerol-protein kinase system, the phospholipase A2-arachidonic acid/prostanoids/leukotrienes system→changes in functional activity induced by second messenger systems other than NMDA receptor/$Ca^{++}$/$Ca^{++}$-calmodulin/protein kinase systems; and, f) interactions with other excitatory amino acid receptor subtypes including non-NMDA receptors and metabotropic receptors as well as intracellular events subsequent to the activation of these excitatory amino acid receptor subtypes→changes in functional activity induced by the non-NMDA and metabotropic receptor activation.

A substance that blocks the NMDA receptor will effectively prevent all of the foregoing major intracellular sequences of events from taking place. However, even with activation of the NMDA receptor, it is still possible to treat pain in accordance with this invention by administering the non-narcotic analgesic and a substance that blocks at least one of the foregoing major intracellular sequences of events. Thus, e.g., a substance that interferes with translocation and activation of protein kinase C or with calmodulin induced activation of constitutive nitric oxide synthase as well as induction of inducible nitric oxide synthase is also useful for the practice of this invention.

Nontoxic substances that block a major intracellular consequence of NMDA receptor activation and are therefore useful in the practice of the invention include inhibitors of protein kinase C, e.g., gangliosides such as ganglioside $GM_1$ (monosialoganglioside) and ganglioside $GT_{1b}$ (trisialoganglioside); amphipathic long chain bases such as sphingosine, N,N,N-trimethylsphingosine, sphinganine and psychosine; quinolyloxazole-2-ones such as 4-methyl-5-(3-quinolinyl)-2-(3H)-oxazolone and phenyl-5-(2-quinolinyl)-2-3(3H)-oxazolone; 1,4-bis-(aminohydroxyalkylamino)-anthraquinones such as 1,4-bis-(3-propylamino-2-hydroxypropylamino)-9,10 anthracenedione and 1,4-bis-(3-benzylamino-2-hydroxypropylamino)-9,10 anthracenedione; and, mixtures and pharmaceutically acceptable salts of any of the foregoing.

Additional nontoxic substances that block a major intracellular consequence of NMDA receptor activation and as such are useful in the practice of the invention include inhibitors of calmodulin such as the phenothiazines, in particular, chlorpromazine, chlorpromazine sulfoxide, prochlorperazine dimaleate, perphenazine, trifluoperazine, fluphenazine, fluphenazine enanthate, fluphenazine decanoate, thioridazine, mesoridazine besylate, piperacetazine, acetophenazine dimaleate, carphenazine dimaleate, butaperazine dimaleate and phenothiazine sulfoxide; naphthalenesulfonamides such as N-(6-aminohexyl)-5-chloro-1-naphthalenesulfonamide, N-(6-aminohexyl)-5-chloro-2-naphthalenesulfonamide and N-(6-aminohexyl)-5-bromo-2-naphthalenesulfonamide; 4-substituted-4H,6H-pyrrolo[1,2-a][4,1] benzoxazepines such as 1,3-dihydro-1-{1-[(4-methyl-4H,6H-pyrrolo[1,2-a][4,1] benzoxazepin-4-yl)methyl]-4-piperidinyl}-2H-benzimidazol-2-one; benzhydryls such as N-[2](diphenylmethylthioethyl]-2-(trifluoromethyl)benzeneethanamine, N-[2-(bis(4-fluorophenyl)methylthio)ethyl]-2-(trifluoromethyl) benzeneethanamine and N-[2-(bis(4-fluorophenyl)methylthio)ethyl]-3-(trifluoromethyl)benzeneethanamine; tricyclic antidepressant drugs such as imipramine, 2-chloroimipramine and amitriptyline; penfluridol; haloperidol; pimozide; clozapine; calmidazolin; and, mixtures and pharmaceutically acceptable salts of any of the foregoing.

Of the two groups of analgesia enhancers, the NMDA-receptor antagonists are preferred and of these, dextromethorphan is preferred for the reasons previously stated.

To exhibit its analgesic activity-enhancing effect, the nontoxic NMDA receptor antagonist and/or substance that blocks a major intracellular consequence of NMDA receptor activation must be present in an analgesia enhancing amount. This amount can be experimentally determined for a given substance of this type by those skilled in the art employing routine dosage determination procedures in view of the experimental data herein. In the case of the NMDA receptor antagonist dextromethorphan, a usual recommended dose for adult humans would be at least about 15 mg and preferably at least about 20 mg. Unit dosages can contain less than these amounts of dextromethorphan provided, of course, sufficient multiples of the unit dose are administered at one time to provide the aforestated minimum dextromethorphan dose. Thus, e.g., one or two tablets each containing 325 mg aspirin (or other analgesic) and 15 mg dextromethorphan can be administered at one time (up to 4 times in a 24 hour period) to provide enhanced analgesia in accordance with the present invention.

Dosage levels for the NSAID will, of course, be those sufficient to induce an effective degree of analgesia. Thus, e.g., for adult humans, typical unit dosage levels can be from about 50 to about 650 mg for aspirin, from about 125 to about 500 mg for diflunisal, from about 25 to about 100 mg for zomepirac sodium, from about 50 to about 400 mg for ibuprofen, from about 125 to about 500 mg for naproxen, from about 25 to about 50 mg for flurbiprofen, from about 60 to about 200 mg for fenoprofen, from about 10 to about 20 mg for piroxicam, from about 125 to about 250 mg for mefenamic acid, from about 100 to about 400 mg for fenbufen and from about 25 to about 50 mg for ketoprofen. Dosage levels for the NSAID which are greater or lesser than these can, of course, be employed if desired.

While the NSAID and the analgesia enhancer need not be administered together, they must both be present in the patient at effective levels at the same time. While it is within the scope of the invention to administer the NSAID and analgesia enhancer separately, as a matter of convenience, it is preferred that they be coadministered as a single therapeutic composition. All modes of administrations are contemplated, e.g., administration can be orally, rectally or by intravenous, intramuscular, subcutaneous, intrathecal, epidural or intracerebroventricular injection.

The therapeutic composition containing the NSAID and the analgesia enhancer will ordinarily be formulated with one or more pharmaceutically acceptable ingredients in accordance with known and established practice. Thus, the composition can be formulated as a liquid, powder, elixir, injectable solution, etc. Formulations for oral use can be provided as tablets or hard capsules wherein the pharmacologically active ingredients are mixed with an inert solid diluent such as calcium carbonate, calcium phosphate or kaolin, or as soft gelatin capsules wherein the active ingredients are mixed with an oleaginous medium, e.g., liquid paraffin or olive oil.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene exide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monooleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

The pain-alleviating therapeutic composition of this invention is advantageously provided in sustained release dosage form of which many kinds are known, e.g., as described in U.S. Pat. Nos. 4,788,055; 4,816,264; 4,828,836; 4,834,965; 4,834,985; 4,996,047; 5,071,646; and, 5,133,974, the contents of which are incorporated by reference herein. In addition to the NSAID (a) and analgesia enhancer (b), the therapeutic composition herein can contain at least one other pharmacologically active substance (c), e.g., a narcotic analgesic such as codeine or a local anesthetic such as lidocaine, dibucaine or bupivicaine (where the composition is provided as an injectable).

The following are typical unit dosage forms of the therapeutic composition of this invention.

| Unit Dosage Form | Non-narcotic Analgesic | mg | Analgesia Enhancer | mg | No. of Unit Doses per Administration |
|---|---|---|---|---|---|
| tablet | aspirin | 325 | dextromethorphan HBr | 15 | 2 |
| tablet | aspirin | 650 | dextromethorphan HBr | 30 | 1 |
| tablet | diflusinal | 250 | dextromethorphan HBr | 15 | 2 |
| tablet | diflusinal | 500 | dextromethorphan HBr | 30 | 1 (maintenance dosage) or 2 (initial dosage) |
| tablet | phenylbutazone | 100 | dextromethorphan HBr | 30 | 1 |
| capsule | phenylbutazone | 100 | dextromethorphan HBr | 30 | 1 |
| capsule | indomethacin | 25 | dextromethorphan HBr | 15 | 2 |
| capsule | indomethacin | 50 | dextromethorphan HBr | 30 | 1 |
| suppository | indomethacin | 50 | dextromethorphan HBr | 30 | 1 |
| oral suspension | indomethacin | 25/5 ml | dextromethorphan HBr | 15 | 2 |
| tablet | sulindac | 150 | dextromethorphan HBr | 30 | 1 |
| tablet | sulindac | 200 | dextromethorphan HBr | 30 | 1 |
| capsule | mefenamic acid | 250 | dextromethorphan HBr | 30 | 1 (maintenance dosage) or 2 initial dosage) |
| capsule | meclofenamate sodium | 50 | dextromethorphan HBr | 30 | 1 |
| tablet | tolmetin sodium | 200 | dextromethorphan HBr | 30 | 1 |
| tablet | ibuprofen | 200 | dextromethorphan HBr | 15 | 2 |
| tablet | ibuprofen | 800 | dextromethorphan HBr | 30 | 1 |
| tablet | ibuprofen | 800 | dextromethorphan HBr | 40 | 1 |
| tablet | naproxen | 250 | dextromethorphan HBr | 15 | 2 |
| tablet | naproxen | 250 | dextromethorphan HBr | 30 | 1 |
| oral suspension | naproxen | 125/5 ml | dextromethorphan HBr | 15 | 2 |
| tablet | naproxen sodium | 275 | dextromethorphan HBr | 30 | 1 |
| capsule | fenaprofen calcium | 200 | dextromethorphan HBr | 15 | 2 |
| capsule | ketoprofen | 25 | dextromethorphan HBr | 15 | 2 |
| capsule | ketoprofen | 75 | dextromethorphan HBr | 30 | 1 |
| tablet | flurbiprofen | 100 | dextromethorphan HBr | 15 | 2 |
| tablet | flurbiprofen | 10 | dextromethorphan HBr | 30 | 1 |
| capsule | piroxicam | 20 | dextromethorphan HBr | 30 | 1 |
| capsule | piroxicam | 25 | dextromethorphan HBr | 30 | 1 |
| tablet | diclofenac sodium | 25 | dextromethorphan HBr | 15 | 2 |
| tablet | diclofenac sodium | 75 | dextromethorphan HBr | 30 | 1 |

The following example is illustrative of the method and composition of the invention in alleviating arthritic pain induced in the Sprague-Dawley rat.

EXAMPLE

A. Test Procedures

Arthritic pain (monarthritis) was induced in the rats by intracapsual injection of a complete adjuvant (Butler et al., *Pain*, 48 (1992), pp. 73–81). The complete adjuvant was made up of 60 mg killed *Mycobacterium butyricum* in a mixture of paraffin oil (6 ml), 0.9% NaCl (4 ml) and Tween 80 (1 ml). The rats were briefly anesthetized with isoflurane administered in a mixed $N_2O/O_2$ gas. A drop of complete adjuvant (about 0.05 ml) was injected into the ankle (tarsotibial) joint with a 26 gauge needle. Monarthritic pain develops in about 7 days after injection and peaks after about two weeks (Butler et al., ibid.).

The following behavioral tests of arthritic pain were made at 12 days after the injection of complete adjuvant to establish baseline scores for each test as described in the literature (Butler et al., ibid.; Perrot et al., *Pain*, 52 (1993), pp. 41–47).

(1) Mechanical Hyperalgesia

The Randall-Selitto test was used to examine mechanical hyperalgesia (Butler et al., ibid.; Perrot et al., ibid.). A graded mechanical force (in grams) delivered through the Randall-Selitto device was applied to the affected and unaffected ankle areas. A rat withdrew its hindpaw or vocalized when the applied force reached its pain threshold. This force was recorded to indicate the degree of mechanical hyperalgesia.

(2) Spontaneous Pain-related Behavior (Paw Lifting)

Each rat was permitted to move freely without restraint within an open-top plexiglass cylinder (diameter 19 cm×height 30 cm) and was habituated to the cylinder for 5 min before the observation. Within a 10 min observation period, the total duration (in seconds) over which a rat lifted its arthritic paw was recorded.

(3) Joint Stiffness Score

Restriction of full range of flexion or extension of the injected joint was examined. The injected joint was gently flexed or extended to the point where the rat resisted further movement of the tested joint. In an arthritic rat, the maximal joint stiffness score is two points if restriction on the full range movement of both flexion and extension of the affected joint is present.

After determination of the baseline scores for each of these three tests, each rat received a single intraperitoneal or oral administration with one of the following test substances: (1) ibuprofen alone, (2) dextromethorphan HBr alone, (3) a combination of ibuprofen and dextromethorphan HBr or (4) saline (control) alone. At one hour (intraperitoneal) or two hours (oral) after each administration, the behavioral tests described above were repeated to examine the effects of each test substance on arthritic pain.

B. Test Results

FIGS. 1–6 present the results of the foregoing tests. FIGS. 1–3 and 4–6 present the results of intraperitoneal injection and oral administration (n=5–6/group), respectively.

Figure 1:
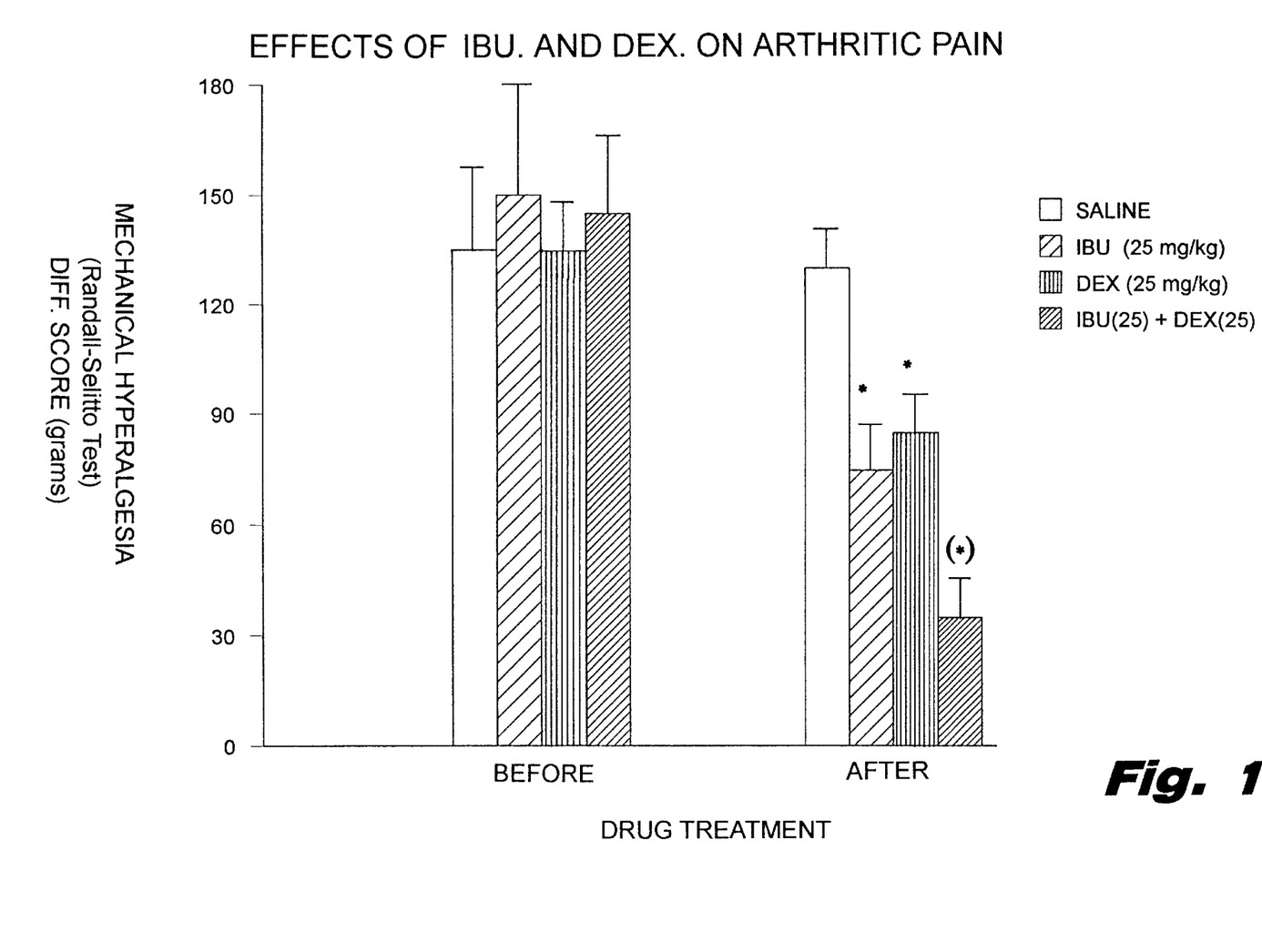
FIG. 1 is a bar graph comparing the difference scores for mechanical hyperalgesia, an indicator of arthritic pain, observed in laboratory animals with induced arthritis both before and following the administration by percutaneous injection of each of several test substances.

FIG. 1: Mechanical Hyperalgesia—Intraperitoneal Administration

The difference scores (unaffected hindpaw minus affected hindpaw) reflecting the force (grams) applied to the ankle joint area which produces vocalization and paw-withdrawal were used to express the degree of mechanical hyperalgesia. Difference scores were not different before administration of the test substances among the groups. When tested at one hour after administration of the test substances, difference scores were reliably reduced in rats receiving a single intraperitoneal injection of 25 mg/kg ibuprofen or 25 mg/kg dextromethorphan HBr as compared to the saline controls. A combined intraperitoneal injection of ibuprofen and dextromethorphan HBr (25 mg/kg each) resulted in significantly greater reduction of difference scores than that obtained after ibuprofen or dextromethorphan HBr administration alone indicating a significantly enhanced therapeutic effect for the combination of ibuprofen and dextromethorphan HBr. *=P<0.05, Waller-Duncan K ratio t test ("SAS Procedures Guide", Version 6, 34d ed., SAS Institute Inc., Cary, N.C. (1990), pp. 705 et seq. Mao et al., *Brain Res.*, 576, (1997), pp. 254–262) as compared to the saline controls. (*)= P<0.05, Waller-Duncan K ratio t test, as compared to the ibuprofen or dextromethorphan HBr alone group and the saline controls.

Figure 2:
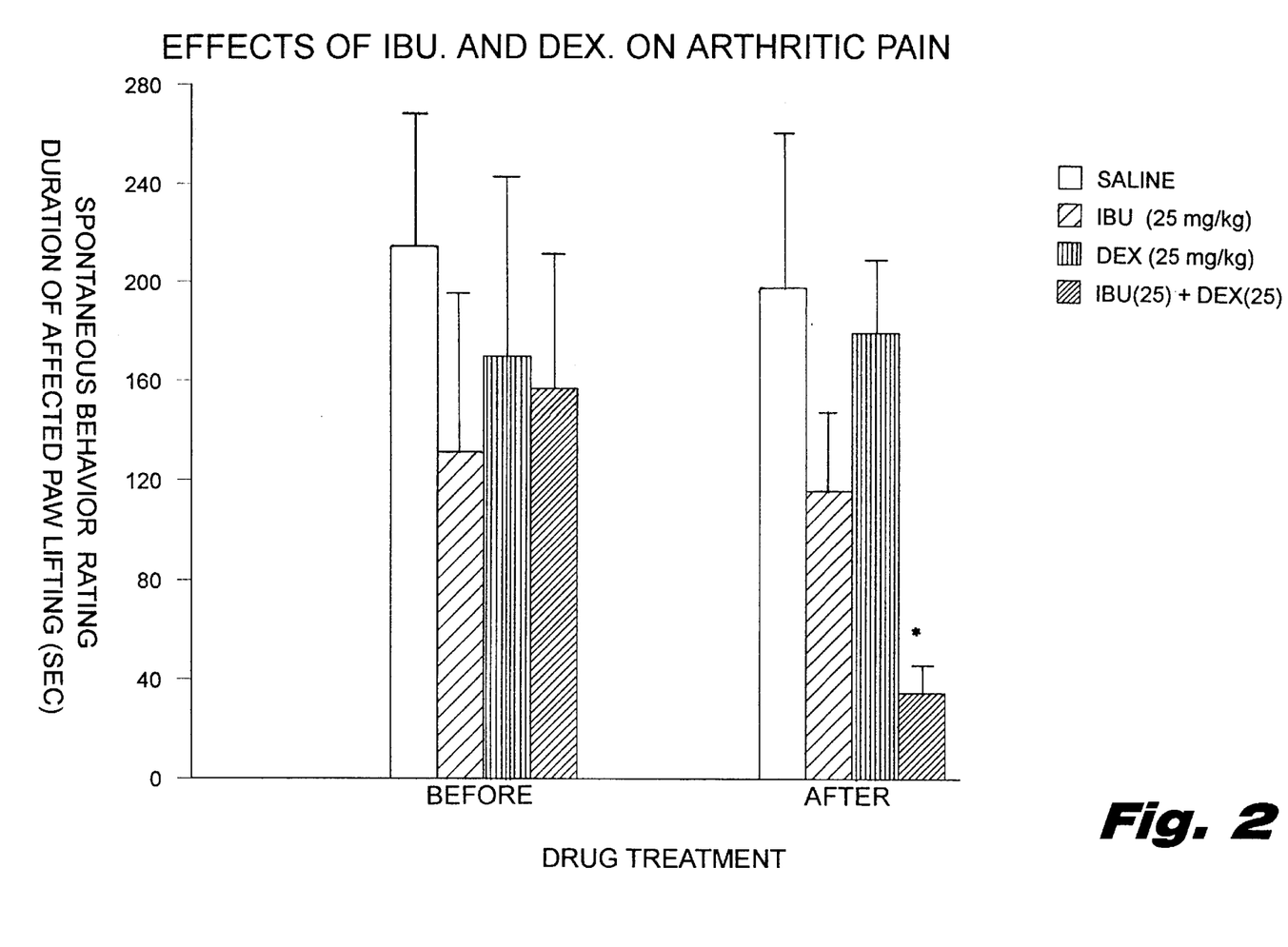
FIG. 2 is a bar graph comparing the spontaneous pain-related behaviors ratings (duration of affected paw lifting), another indicator of arthritic pain, observed for the animals both before and following injection with each of the test substances.

FIG. 2: Spontaneous Pain-related Behaviors Intraperitoneal Administration

Duration (in seconds) of both affected and unaffected hindpaws lifting from the surface over a 10 min observation period was recorded indicating the presence of spontaneous arthritic pain. While the tested rats did not lift the unaffected hindpaw during the observation period, they frequently lifted the affected hindpaw before drug administration. A combined intraperitoneal injection of ibuprofen and dextromethorphan HBr (25 mg/kg each), but not the two substances (25 mg/kg each) given separately, significantly reduced the duration of lifting of the affected hindpaw when observed at one hour after administration. *=P<0.05, Waller-Duncan K ratio t test, as compared to the ibuprofen or dextromethorphan HBr alone group and the saline controls.

Figure 3:
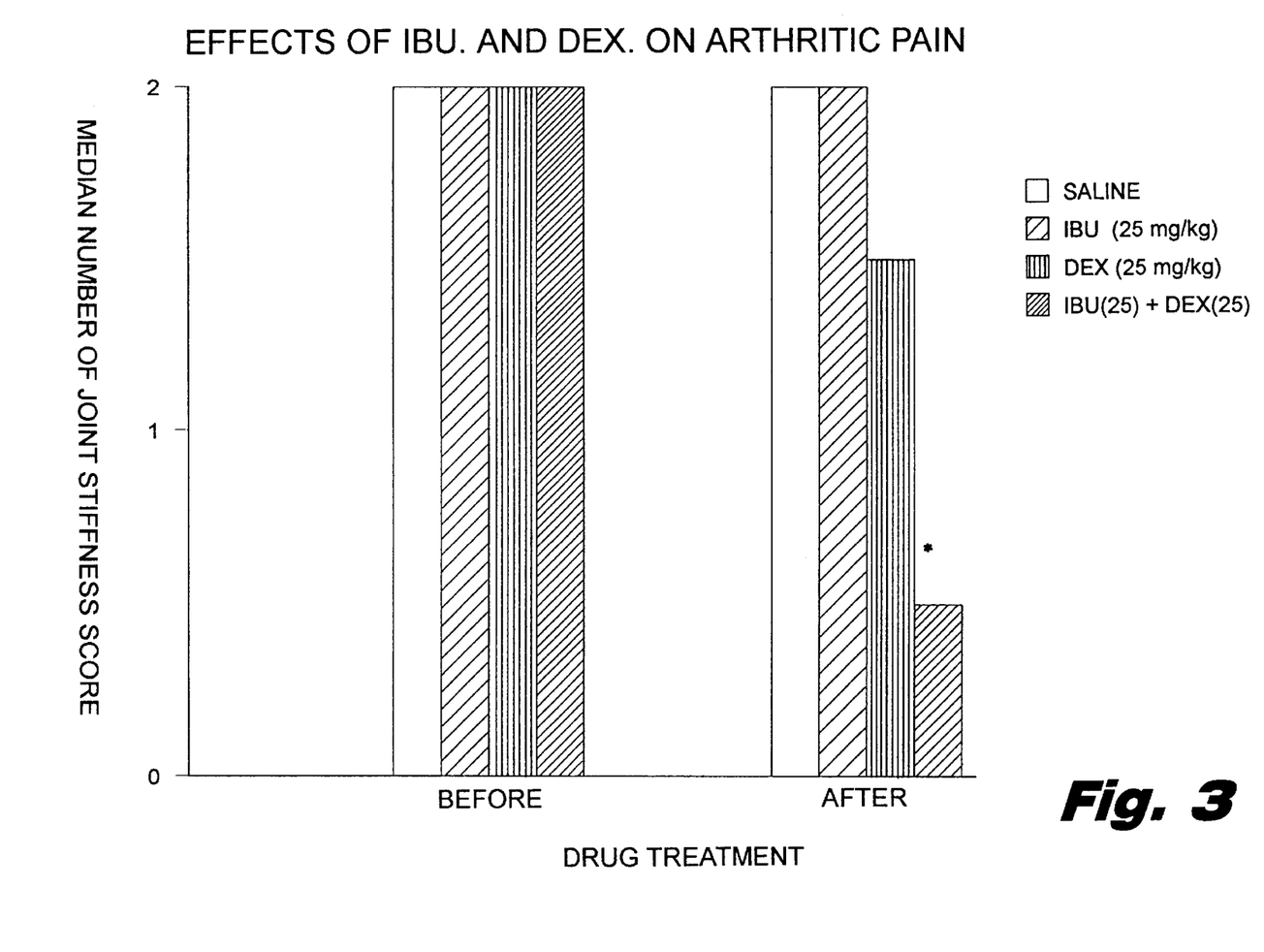
FIG. 3 is a bar graph comparing the median number of joint stiffness scores, yet another indicator of arthritic pain, in the animals both before and following injection with each of the test substances.

FIG. 3: Joint Stiffness—Intraperitoneal Administration

Restriction on the full range of either flexion or extension of the affected joint was scored as one point. In an arthritic rat, the maximal joint stiffness score is two points if restriction on the full range of movement of both flexion and extension of the affected joint is present. The median number of these scores are shown in FIG. 3. Joint stiffness was shown during both flexion and extension of the affected hindpaw before drug treatment. A combined intraperitoneal injection of ibuprofen and dextromethorphan HBr (25 mg/kg each), but not the two substances (25 mg/kg each) administered separately, significantly reduced joint stiffness scores when tested at one hour after administration indicating a significant reduction in of joint stiffness in the affected joint. *=P<0.05, Mann-Whitney U test, ("SAS Procedures Guide", ibid.; Mao et al., ibid.), as compared to the ibuprofen or dextromethorphan HBr alone group and saline controls.

Figure 4:
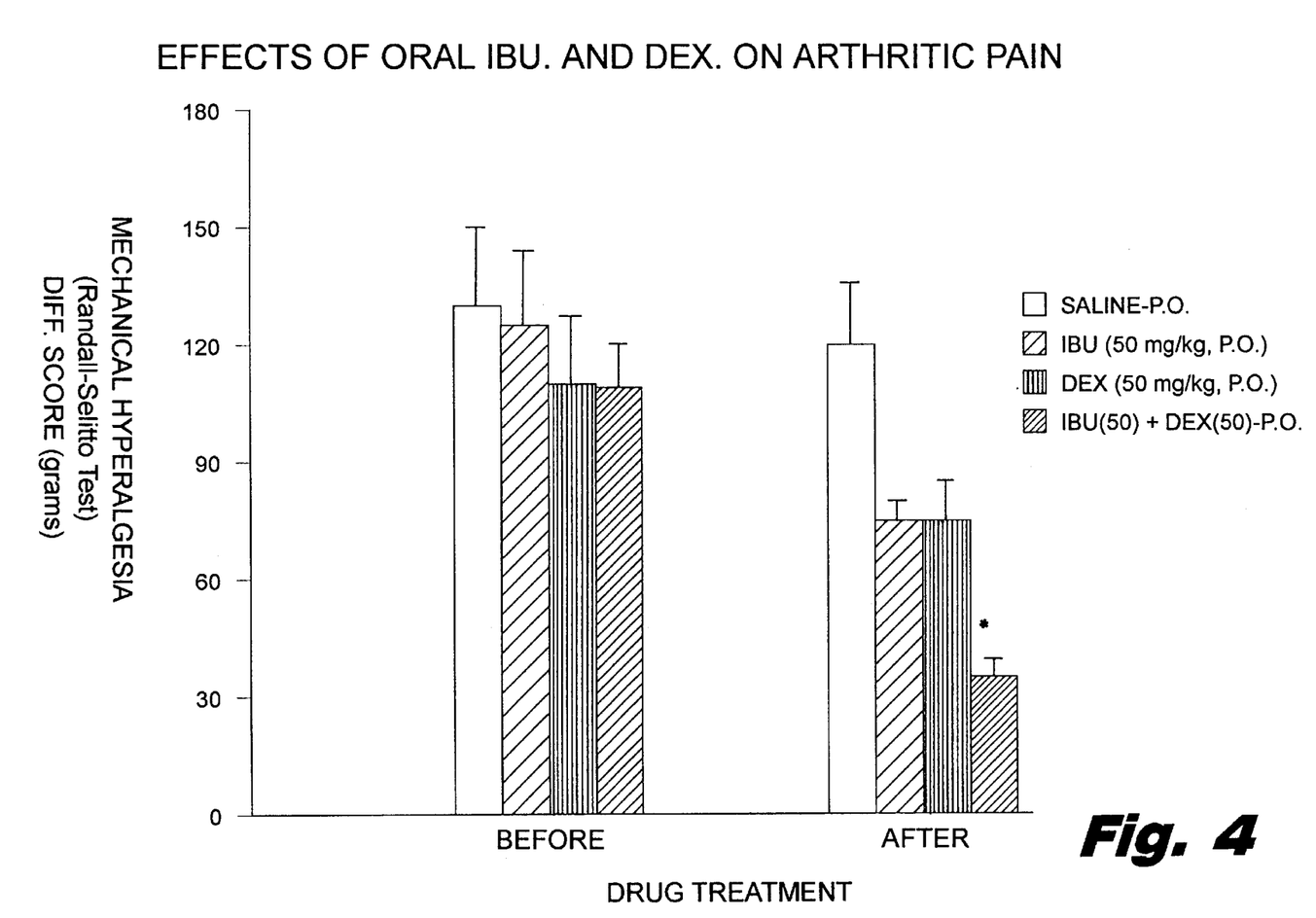
FIG. 4 is a bar graph comparing the difference scores in the animals for mechanical hyperalgesia both before and following oral administration of each of the test substances.

FIG. 4: Mechanical Hyperalgesia—Oral Administration

Difference scores were not different before the administration of the test substances among all groups. A combined single oral administration of ibuprofen and dextromethorphan Hbr (50 mg/kg each), but not the two substances (50 mg/kg each) given separately, resulted in a significant reduction in the difference scores when tested at two hours after administration indicating a significantly enhanced level of analgesia for the combination of ibuprofen and dextromethorphan HBr compared with the other test substances. *=P<0.05, Waller-Duncan K ratio t test, as compared to the saline controls.

Figure 5:
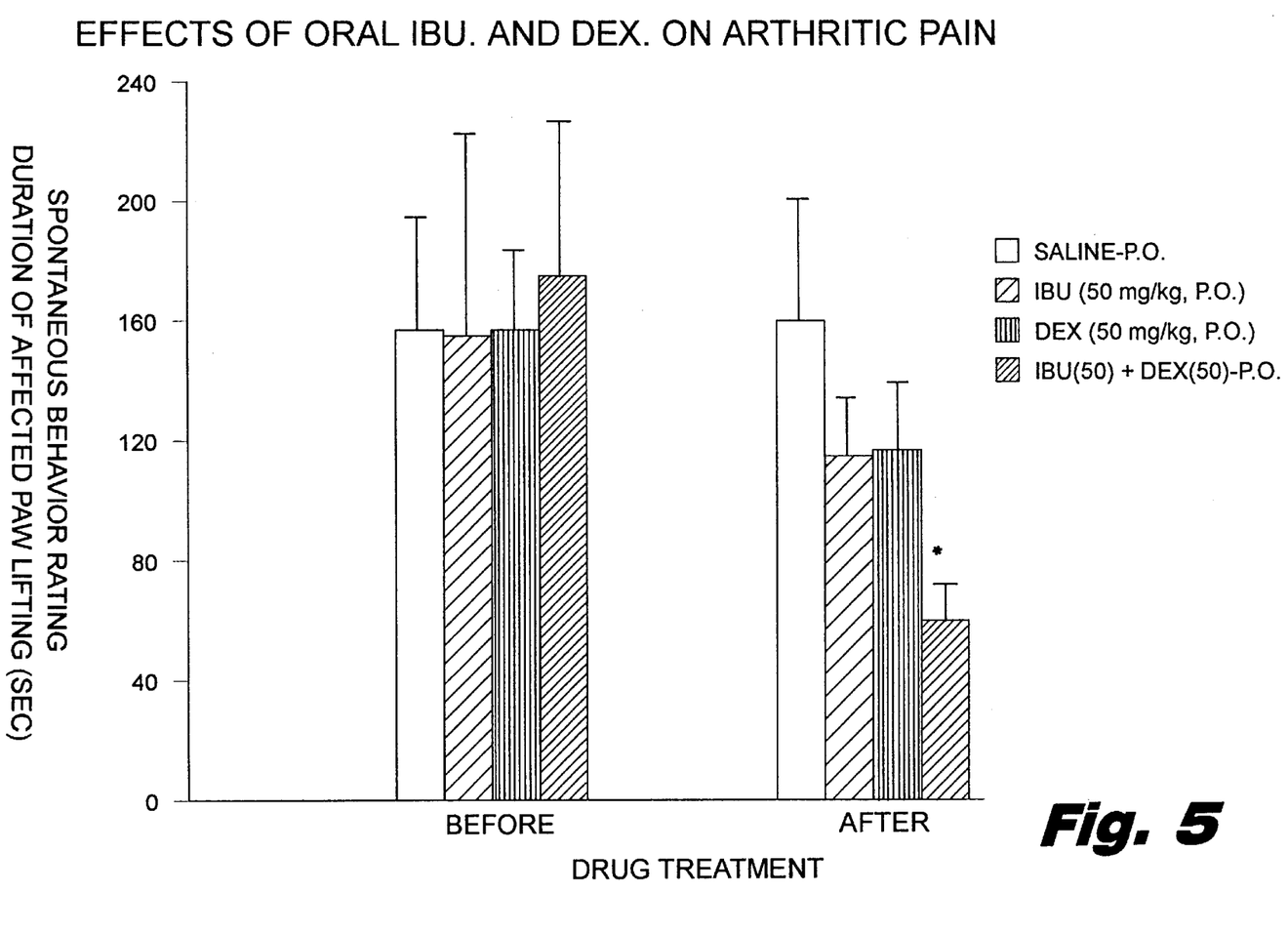
FIG. 5 is a bar graph comparing the spontaneous pain-related behaviors ratings for the animals both before and following oral administration of each of the test substances; and, FIG. 6 is a bar graph comparing the median number of joint stiffness scores in the animals both before and following oral administration of each of the test substances.

FIG. 5: Spontaneous Pain-related Behaviors—Oral Administration

While the tested rats did not lift the unaffected hindpaw during the observation period, they frequently lifted the affected hindpaw before drug administration. A combined single oral administration of ibuprofen and dextromethorphan HBr (50 mg/kg each), but not the two substances (50 mg/kg each) given separately, significantly reduced the duration of lifting of the affected hindpaw when observed at two hours after administration. *=P<0.05, Waller-Duncan K ratio t test, as compared to saline controls.

Figure 6:
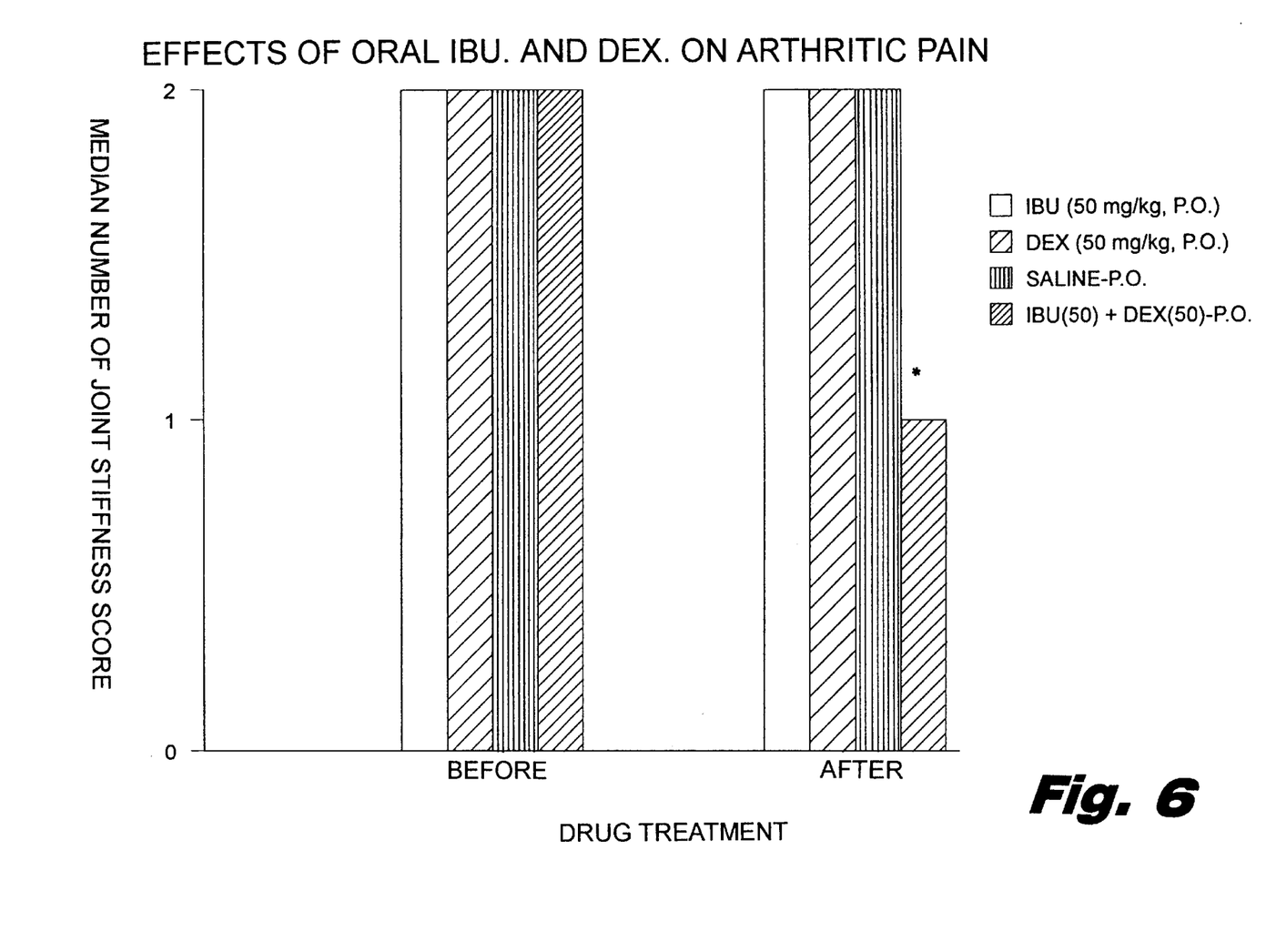

FIG. 6: Joint Stiffness—Oral Administration

The median number of these scores are presented in FIG. 6. Joint stiffness is shown during both flexion and extension of the affected hindpaw before administration of the test substances. A combined single oral administration of ibuprofen and dextromethorphan HBr (50 mg/kg each), but not the two substances (50 mg/kg each) given separately, significantly reduced joint stiffness scores when tested at two hours after administration indicating a significant reduction in joint stiffness in the affected joint. *=P<0.05, Mann-Whitney U test, as compared to the ibuprofen or dextromethorphan HBr alone group and saline controls.

What is claimed is:

1. A method of alleviating pain which comprises administering to a mammal exhibiting pain but not exhibiting a cold, influenza, cough, mouth pain and/or dysmenorrhea condition (a) an analgesia-inducing amount of an NSAID selected from the group consisting of ibuprofen, aspirin, diclofenac, etodolac, ketorolac, naproxen, piroxicam and pharmaceutically acceptable salt thereof and (b) an analgesia enhancing amount of at least one analgesia enhancer selected from the group consisting of dextromethorphan, dextrorphan and pharmaceutically acceptable salt thereof with (a) being administered prior to, with or following the administration of (b).

2. The method of claim 1 wherein (a) and (b) are coadministered as a sustained release dosage form.

3. The method of claim 1 wherein at least about 15 mg/dose of (b) is administered.

4. The method of claim 1 wherein at least about 20 mg/dose of (b) is administered.

5. The method of claim 1 wherein the pain is associated with an active site of inflammation.

6. The method of claim 1 wherein the pain is arthritic pain, lumbosacral pain, musculoskeletal pain or pain of sore throat.

* * * * *